(12) United States Patent
Procyk

(10) Patent No.: US 10,493,223 B2
(45) Date of Patent: Dec. 3, 2019

(54) DETERMINING OF SUBJECT ZERO FLOW USING CLUSTER ANALYSIS

(71) Applicant: KONINKLIJKE PHILIPS N.V., Eindhoven (NL)

(72) Inventor: Christopher Anthony Procyk, New Kensington, PA (US)

(73) Assignee: Koninklijke Philips N.V., Eindhoven (NL)

( * ) Notice: Subject to any disclaimer, the term of this patent is extended or adjusted under 35 U.S.C. 154(b) by 980 days.

(21) Appl. No.: 14/898,559

(22) PCT Filed: Jun. 5, 2014

(86) PCT No.: PCT/IB2014/061961
§ 371 (c)(1),
(2) Date: Dec. 15, 2015

(87) PCT Pub. No.: WO2014/203104
PCT Pub. Date: Dec. 24, 2014

(65) Prior Publication Data
US 2016/0151590 A1    Jun. 2, 2016

Related U.S. Application Data

(60) Provisional application No. 61/836,771, filed on Jun. 19, 2013.

(51) Int. Cl.
*A61M 16/00* (2006.01)
*A61B 5/00* (2006.01)
(Continued)

(52) U.S. Cl.
CPC .... *A61M 16/0051* (2013.01); *A61M 16/0069* (2014.02); *A61M 16/026* (2017.08);
(Continued)

(58) Field of Classification Search
CPC .............. A61M 16/00; A61M 16/0051; A61M 16/0066; A61M 16/0069; A61M 16/022;
(Continued)

(56) References Cited

U.S. PATENT DOCUMENTS

| | | | | |
|---|---|---|---|---|
| 5,148,802 A * | 9/1992 | Sanders | .............. | A61M 16/026 128/204.18 |
| 6,257,234 B1 * | 7/2001 | Sun | ..................... | A61M 16/026 128/204.18 |

(Continued)

FOREIGN PATENT DOCUMENTS

| EP | 2111790 A1 | 10/2009 |
|---|---|---|
| WO | WO0228460 A1 | 4/2002 |
| WO | WO2006008745 A2 | 1/2006 |

OTHER PUBLICATIONS

"The Weighted Mean", retrieved from https://web.archive.org/web/20080828183728/https://ned.ipac.caltech.edu/leve15/Leo/Stats4_5.html with date Aug. 28, 2008.*

(Continued)

*Primary Examiner* — Joseph D. Boecker
(74) *Attorney, Agent, or Firm* — Michael W. Haas

(57) ABSTRACT

Systems and method for determining zero subject flow rate for correcting leak estimation in respiratory devices. Estimating leak in respiratory devices is necessary for proper ventilation of the subject. Correctly estimating leak allows synchronous triggering and enables accurate measurements of respiratory parameters such as tidal volumes and peak flows to be performed. The systems (10) and the method (100) herein provide a solution to correct (116) for errors in leak estimation methods through analysis (108, 110, 112) of flow rate of the pressurized flow of breathable gas generated (104) by a pressure generator (12) of a respiratory device, and identification or estimation (114) of the flow rate of the pressurized flow at which zero subject flow rate occurs, (Continued)

wherein adjustments to the employed leak estimation method can be thereafter made. The analysis and determination or estimation involve clustering methods, in particular analysis of a histogram of flow rate parameter values determined for individual sampling intervals, wherein the flow rate parameter value corresponding to zero subject flow rate is determined on the basis of the histogram and may involve determining a histogram bin or range value having the highest number of flow rate parameter values or mode of the histogram.

12 Claims, 4 Drawing Sheets

(51) Int. Cl.
 *A61B 5/087* (2006.01)
 *A61M 16/06* (2006.01)
 *A61B 5/08* (2006.01)
(52) U.S. Cl.
 CPC .............. *A61B 5/087* (2013.01); *A61B 5/0816* (2013.01); *A61B 5/7246* (2013.01); *A61M 16/0066* (2013.01); *A61M 16/06* (2013.01); *A61M 2016/0015* (2013.01); *A61M 2016/0033* (2013.01); *A61M 2205/15* (2013.01); *A61M 2205/3303* (2013.01); *A61M 2205/3334* (2013.01); *A61M 2205/3365* (2013.01); *A61M 2205/50* (2013.01); *A61M 2205/52* (2013.01); *A61M 2230/40* (2013.01); *A61M 2230/42* (2013.01)
(58) Field of Classification Search
 CPC .. A61M 16/024; A61M 16/026; A61M 16/06; A61M 2016/0015; A61M 2016/0018; A61M 2016/0021; A61M 2016/003; A61M 2016/0033; A61M 2016/0036; A61M 2016/0039; A61M 2205/15; A61M 2205/3334; A61M 2205/52; A61M 2230/42; G01M 3/2846; A61B 5/0816; A61B 5/087; A61B 5/7246
 See application file for complete search history.

(56) References Cited

U.S. PATENT DOCUMENTS

| | | | |
|---|---|---|---|
| 2002/0023645 A1* | 2/2002 | Zdrojkowski | A61M 16/026 128/204.23 |
| 2002/0053345 A1* | 5/2002 | Jafari | A61M 16/00 128/204.23 |
| 2002/0069874 A1* | 6/2002 | Berthon-Jones | A61M 16/0057 128/202.22 |
| 2006/0070624 A1 | 4/2006 | Kane | |
| 2008/0319333 A1* | 12/2008 | Gavish | A61B 7/003 600/529 |
| 2009/0306530 A1 | 12/2009 | Platt | |
| 2010/0101574 A1* | 4/2010 | Bassin | A61M 16/0051 128/204.21 |
| 2011/0303223 A1* | 12/2011 | Kane | A61M 16/00 128/204.23 |
| 2012/0078542 A1* | 3/2012 | Younes | A61M 16/0051 702/51 |
| 2013/0116942 A1* | 5/2013 | Hill | A61M 16/026 702/51 |
| 2013/0118496 A1* | 5/2013 | Truschel | A61M 16/0051 128/204.23 |
| 2013/0317765 A1* | 11/2013 | Rao | A61M 16/0051 702/51 |
| 2014/0007878 A1* | 1/2014 | Armitstead | A61B 5/083 128/204.23 |

OTHER PUBLICATIONS

"Constructing a Histogram", retrieved from https://web.archive.org/web/20100924034122/http://www.oswego.edu/~srp/stats/hist_con.htm with date Sep. 24, 2010.*

Histograms: Construction, Analysis and Understanding; retrieved from https://web.archive.org/web/20121213134346/http://quarknet.fnal.gov/toolkits/new/histograms.html with date Dec. 13, 2012.*

* cited by examiner

DETERMINING OF SUBJECT ZERO FLOW USING CLUSTER ANALYSIS

CROSS-REFERENCE TO RELATED APPLICATIONS

This patent application claims the priority benefit under 35 U.S.C. § 371 of international patent application no. PCT/IB2014/061961, filed Jun. 5, 2014, which claims the priority benefit under 35 U.S.C. § 119(e) of U.S. Provisional Application No. 61/836,771 filed on Jun. 19, 2013, the contents of which are herein incorporated by reference.

BACKGROUND OF THE INVENTION

1. Field of the Invention

The present disclosure pertains to systems and methods for determining the flow rate of pressurized gas generated by a respiratory device corresponding to zero subject flow rate, and in particular, determining the flow rate using cluster analysis techniques.

2. Description of the Related Art

Estimating leak flow in respiratory devices providing pressurized flow of breathable air to a subject is necessary to provide the proper pressure support and ventilation to the airway of the subject during the therapy. An accurate determination of leak allows respiratory devices to effectuate precise synchronous triggering of pressure support functions necessary for a therapy regime, to maintain user comfort, and well as accurately measure respiratory flow parameters of the subject such as tidal volumes and peak flows. As with any form of leak estimation, there are underlying assumptions. When those assumptions are not correct, errors can amount quickly resulting in inaccurate triggering and user discomfort.

Time-domain evaluation methods applied to measured gas parameter values such as flow rate parameter values determined from sensors employed in respiratory devices are typical methods for determining the flow rate corresponding to zero subject flow. Slope analysis is one such method, however is often frustrated by noise, both in the devices control and measurement modules of the device and due to the subjects themselves.

SUMMARY OF THE INVENTION

Accordingly, one or more aspects of the present disclosure relate to a system for determining flow rate of pressurized flow of breathable gas generated in a respiratory device using cluster analysis techniques to provide corrections to leak estimation methods employed by the respiratory device. The flow rate of the pressurized flow corresponding to zero subject flow rate can thereafter be used to make corrections to leak estimation methods employed by respiratory devices. The system comprises a pressure generator configured to generate pressurized flow of breathable gas for delivery to an airway of a breathing subject; one or more sensors configured to generate output signals conveying information related to one or more gas parameters of the pressurized flow of breathable gas; one or more processors configured to execute computer program modules.

The computer program modules comprise, a parameter module configured to determine flow rate parameter values for individual sampling intervals from the output signals of the one or more sensors, the flow rate parameter values indicating flow rate of the pressurized flow of breathable gas during the individual sampling intervals; a grouping module configured to group the flow rate parameter values for sampling intervals during a determination period into flow rate ranges; a quantification module configured to quantify the number of flow rate parameter values per flow rate range during the determination period; and a zero flow rate determination module configured to determine the flow rate parameter value that corresponds to zero subject flow rate based on the quantifications.

Yet another aspect of the present disclosure relates to a method for determining flow rate of pressurized flow of breathable gas generated in a respiratory device using cluster analysis techniques to provide corrections to leak estimation methods employed by the respiratory device. The method comprises the steps of, generating pressurized flow of breathable gas for delivery to an airway of a breathing subject; generating output signals conveying information related to one or more gas parameters of the pressurized flow of breathable gas; determining flow rate parameter values for individual sampling intervals from the output signals, the flow rate parameter values indicating flow rate of the pressurized flow of breathable gas during the individual sampling intervals; grouping the flow rate parameter values for sampling intervals during a determination period into flow rate ranges; quantifying the number of flow rate parameter values per flow rate range during the determination period; and determining the flow rate parameter value that corresponds to zero subject flow rate based on the quantifications.

Still another aspect of present disclosure relates to a system for determining flow rate of pressurized flow of breathable gas generated in a respiratory device using cluster analysis techniques to provide corrections to leak estimation methods employed by the respiratory device. The system comprises means for generating pressurized flow of breathable gas for delivery to an airway of a breathing subject; means for generating output signals conveying information related to one or more gas parameters of the pressurized flow of breathable gas; means for determining flow rate parameter values for individual sampling intervals from the output signals, the flow rate parameter values indicating flow rate of the pressurized flow of breathable gas during the individual sampling intervals; means for grouping the flow rate parameter values for sampling intervals during a determination period into flow rate ranges; means for quantifying the number of flow rate parameter values per flow rate range during the determination period; and means for determining the flow rate parameter value that corresponds to zero subject flow rate based on the quantifications.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
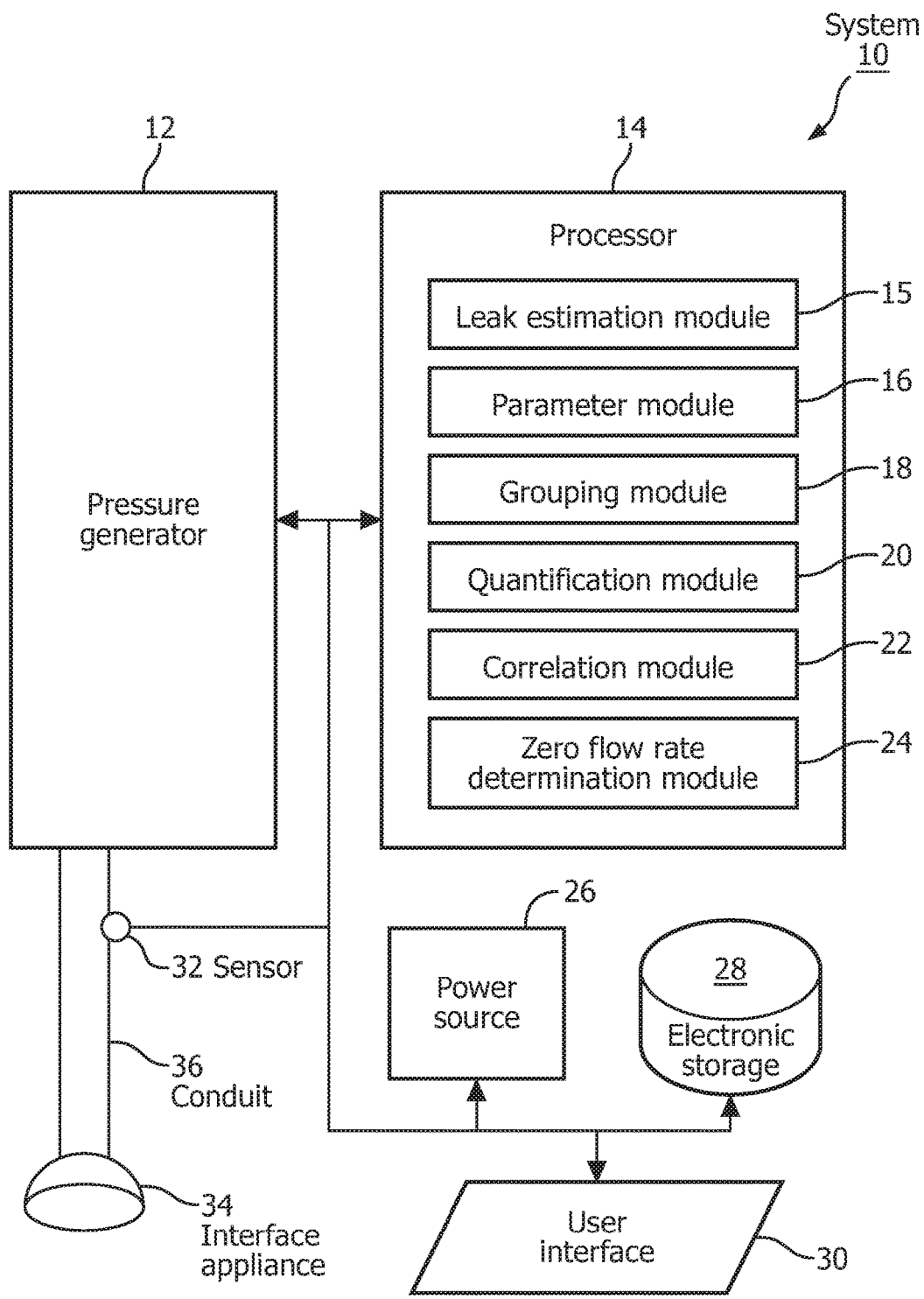
FIG. 1 is a system for determining the flow rate of pressurized flow of breathable gas generated in respiratory devices which corresponds to zero subject flow rate.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 for determining the flow rate of breathable gas generated by a pressure generator 12 at which zero subject flow rate occurs. System 10 is configured to independently determine the flow rate of the pressurized gas generated by pressure generator 12 at which zero subject flow rate occurs using cluster analysis techniques. Gas parameters, such as those related to flow rate of the pressurized flow generated by pressure generator 12, are collected in sampling intervals, and clustered into discrete flow rate ranges. The flow rate ranges are then analyzed to determine a flow rate parameter value corresponding to zero subject flow rate.

Zero subject flow rate is indicated by the transition between a subject's inspiratory flow phase (e.g. inhalation,) and a subsequent expiratory flow phase (e.g., exhalation), transition between a subject's expiratory flow phase (e.g., exhalation) and a subsequent inspiratory flow phase (e.g. inhalation), and/or at an expiratory pause (e.g., pause at the end of an exhalation). Determining the flow rate of pressurized gas generated by pressure generator 12 at which zero subject flow rate occurs allows respiratory devices to correct current leak flow estimations in order to effectuate corrected synchronous triggering of pressure support functions necessary for a therapy regime, to maintain user comfort, and well as accurately measure respiratory flow parameters of the subject such as tidal volumes and peak flows.

The present disclosure contemplates that system 10 may be used to determine zero subject flow rate for subjects employing respiratory ventilation devices such as Continuous Positive Airway Pressure (CPAP) devices, Pressure Assured Volume type devices, and/or for other uses. The other uses may include use with Average Volume Assured Pressure Support (AVAPS) devices, and/or other uses.

In some embodiments, system 10 comprises one or more of pressure generator 12, one or more processors 14, a power source 26, electronic storage 28, a user interface 30, one or more sensors 32, and/or other components.

Pressure generator 12 is configured to generate a pressurized flow of breathable gas for delivery to the airway of a subject. Pressure generator 12 may include a conduit 36 providing a flow path for delivering the breathable gas. Conduit 36 may be integrally connected to an interface appliance 34. Conduit 36 may comprise one or more of a flexible conduit, sealed tubing, and/or other component suitable for delivery of pressurized breathable gas. Interface appliance 34 may comprise one or more of a nasal mask, nasal cannula, a full face mask, a nasal pillow mask, a hybrid mask, an oral mask, a total face mask, an endotracheal tube, and/or other invasive and/or non-invasive interface appliance configured to communicate a flow of pressurized gas within an airway of a subject. In some embodiments, interface appliance 34 may be removably coupled to conduit 36. Interface appliance 34 may be removed for cleaning and/or for other purposes.

Pressure generator 12 generates pressurized flow of breathable gas according to one or more parameters of the flow of gas (e.g., flow rate, pressure, volume, temperature, gas composition, etc.) for therapeutic purposes, and/or for other purposes. By way of a non-limiting example, pressure generator 12 may be configured to generate pressurized flow at a flow rate and/or pressure of the flow of gas to provide pressure support and/or pressure release ventilation to the airway of a subject.

Pressure generator 12 may receive a flow of gas from a gas source, such as the ambient atmosphere, and elevates the pressure of that gas for delivery to the airway of a subject at a pressurized flow. In some embodiments, pressure generator 12 may receive a flow of gas from a gas source through an inlet port (not shown). Pressure generator 12 may be any device, such as, for example, a pump, blower, piston, or bellows, that is capable of elevating the pressure of the received gas for delivery to a subject. Pressure generator 12 may comprise one or more valves for adjusting the delivery of the pressure/flow of gas. The present disclosure also contemplates controlling the operating speed of the blower, either alone or in combination with such valves, to control the pressure/flow of gas provided to the subject.

In some embodiments, pressure generator 12 is configured to supply a pressurized flow of breathable gas in a pressure range of about 4 to 50 $cmH_2O$. In some embodiments, pressure generator 14 may be configured to supply a pressurized flow of breathable gas at other pressures and/or pressure ranges.

One or more sensors 32 are configured to generate output signals conveying information related to one or more parameters of the gas within system 10. The one or more parameters of the gas within system 10 may comprise gas parameters related to the pressurized flow of breathable gas generated by pressure generator 12, breathing parameters related to respiration of the subject employing system 10, and/or other parameters. Sensors 32 may comprise one or more sensors that measure such parameters directly (e.g., through fluid communication with the flow of gas in interface appliance 34, and/or conduit 36). Sensors 32 may comprise one or more sensors that generate surrogate output signals related to the one or more parameters indirectly. For example, sensors 32 may comprise one or more sensors configured to generate an output based on an operating parameter of pressure generator 12 (e.g., patient flow and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of a subject may comprise a tidal volume, a respiratory flow rate, a timing (e.g., start and/or end of inspiratory flow phases, start and/or end of expiratory flow phases, etc.), a respiration rate, a duration (e.g., of inspiratory flow phases, of expiratory flow phases, of a single breathing cycle, etc.), respiration frequency, and/or other breathing parameters.

Although sensors 32 are illustrated at a single location in pressure control ventilation system 10, this is not intended to be limiting. Sensors 32 may comprise sensors disposed in a plurality of locations, such as for example, at various locations within (or in communication with) conduit 36, within pressure generator 12, within (or in communication with) interface appliance 34, and/or other locations.

Processor 14 is configured to provide information processing capabilities in system 10. As such, processor 14 may comprise one or more of a digital processor, an analog processor, a digital circuit designed to process information, an analog circuit designed to process information, a state machine, and/or other mechanisms for electronically processing information. Although processor 14 is shown in FIG. 1 as a single entity, this is for illustrative purposes only. In some implementations, processor 14 may comprise a plurality of processing units. These processing units may be physically located within the same device (e.g., pressure generator 12), or processor 14 may represent processing functionality of a plurality of devices operating in coordination.

As shown in FIG. 1, processor 14 is configured to execute one or more computer program modules. The one or more computer program modules may comprise one or more of a leak estimation module 15, a parameter module 16, a grouping module 18, a quantification module 20, a correlation module 22, a zero flow rate determination module 24, and/or other modules. Processor 14 may be configured to execute modules 15, 16, 18, 20, 22 and/or 24 by software; hardware; firmware; some combination of software, hardware, and/or firmware; and/or other mechanisms for configuring processing capabilities on processor 14.

It should be appreciated that although modules 15, 16, 18, 20, 22 and 24 are illustrated in FIG. 1 as being co-located within a single processing unit, in implementations in which processor 14 comprises multiple processing units, one or more of modules 15, 16, 18, 20, 22 and/or 24 may be located remotely from the other modules. The description of the functionality provided by the different modules 15, 16, 18, 20, 22 and/or 24 described below is for illustrative purposes, and is not intended to be limiting, as any of modules 15, 16, 18, 20, 22 and/or 24 may provide more or less functionality than is described. For example, one or more of modules 15, 16, 18, 20, 22 and/or 24 may be eliminated, and some or all of its functionality may be provided by other modules 15, 16, 18, 20, 22 and/or 24. As another example, processor 14 may be configured to execute one or more additional modules that may perform some or all of the functionality attributed below to one of modules 15, 16, 18, 20, 22 and/or 24.

Leak estimation module 15 is configured to detect ongoing estimation of leak of pressurized flow of breathable gas in system 10. Estimating leak in respiratory devices is necessary for proper ventilation of the subject. Correctly estimating leak allows synchronous triggering and enables accurate measurements of respiratory parameters such as tidal volumes and peak flows to be performed. Leak estimation module 15 may employ a leak estimation algorithm with the following assumptions:

1) A person's expiration volume on a given breath is approximately equal to the inspiratory volume of that breath; and
2) Leaks follows the Bernoulli's orifice flow model, which can be simplified to:

$$Q_{leak} = g_{orf} \cdot P_p^{gamma}$$

Using the above equation, $g_{orf}$ can, according to assumption 1 and with a known gamma, be determined from a full breath by solving for the value of $g_{orf}$ that ensures that patient flow sums to zero over the entire breath.

This method has worked quite well, and continues to work well in most low-leak cases. However, Assumption 1 is under stress due to the popularity of nasal and pillow masks. A patient can inhale through the mask but direct some or all exhalation out their mouth. The second assumption has always been problematical with patients at home, as without being under professional supervision the mask may not be or stay well sealed, and when leaks around the perimeter of the mask occur they do not generally follow known gamma power relationships.

The quality of the leak algorithm can be evaluated if the flow rate of the pressurized gas being generated by the respiratory device at which zero subject flow occurs, can be independently ascertained and then compared to the value established by the above leak estimation algorithm. This would indicate the current quality of the output of the leak estimation algorithm. If errors in the estimation are determined, adjustments to the algorithm can be made to thereafter correctly estimate leak.

When errors in leak estimation occur, triggering is no longer synchronous and the effectiveness of the therapy may be jeopardized. In addition, subject comfort may be affect. System 10 herein provides a solution to correct for errors in the leak estimation method carried out by leak estimation module 15 through analysis of flow rate of the pressurized flow of breathable gas generated by pressure generator 12, and identification of the flow rate of the pressurized flow at which zero subject flow rate occurs, wherein adjustments to the employed leak estimation method can be thereafter made.

In some embodiments, leak estimation module 15 may employ leak estimation algorithms similar to or same as patient disconnect detection algorithms, and/or other algorithm and/or techniques.

Parameter module 16 is configured to determine flow rate parameter values for individual sampling intervals obtained from the output signals of sensors 32. Sampling intervals may be determined in a variety of ways. Sampling intervals may be determined as a function of one or more outputs from one or more sensors 32 related to the subjects breathing patterns and/or determined by one or more parameters of pressure generator 12. Sampling intervals may be predetermined intervals. For example, system 10 may set sampling intervals to sample every 10 milliseconds (or other value).

Sampling intervals may be set by a user. For example, sampling intervals may be set by a care professional, the subject, and/or other user to any desired sampling rate.

Time is further segmented into determination time periods. A determination time period includes multiple sampling periods therein. A determination time period may include an integer multiple of the sampling interval. The determination period may be determined in a variety of ways. The determination period may be a predetermined time period. For example, system 10 may set the determination period to 15 seconds (or other value). The determination period may be set by a user. For example, the determination period may be set by a care professional, the subject, and/or other user to any desired time period duration. The determination period may be dynamically determined per subject. For example, the determination period may be set to the average time it takes the subject to complete two breaths, and/or other amount of breaths, and/or other time duration.

Figure 2:
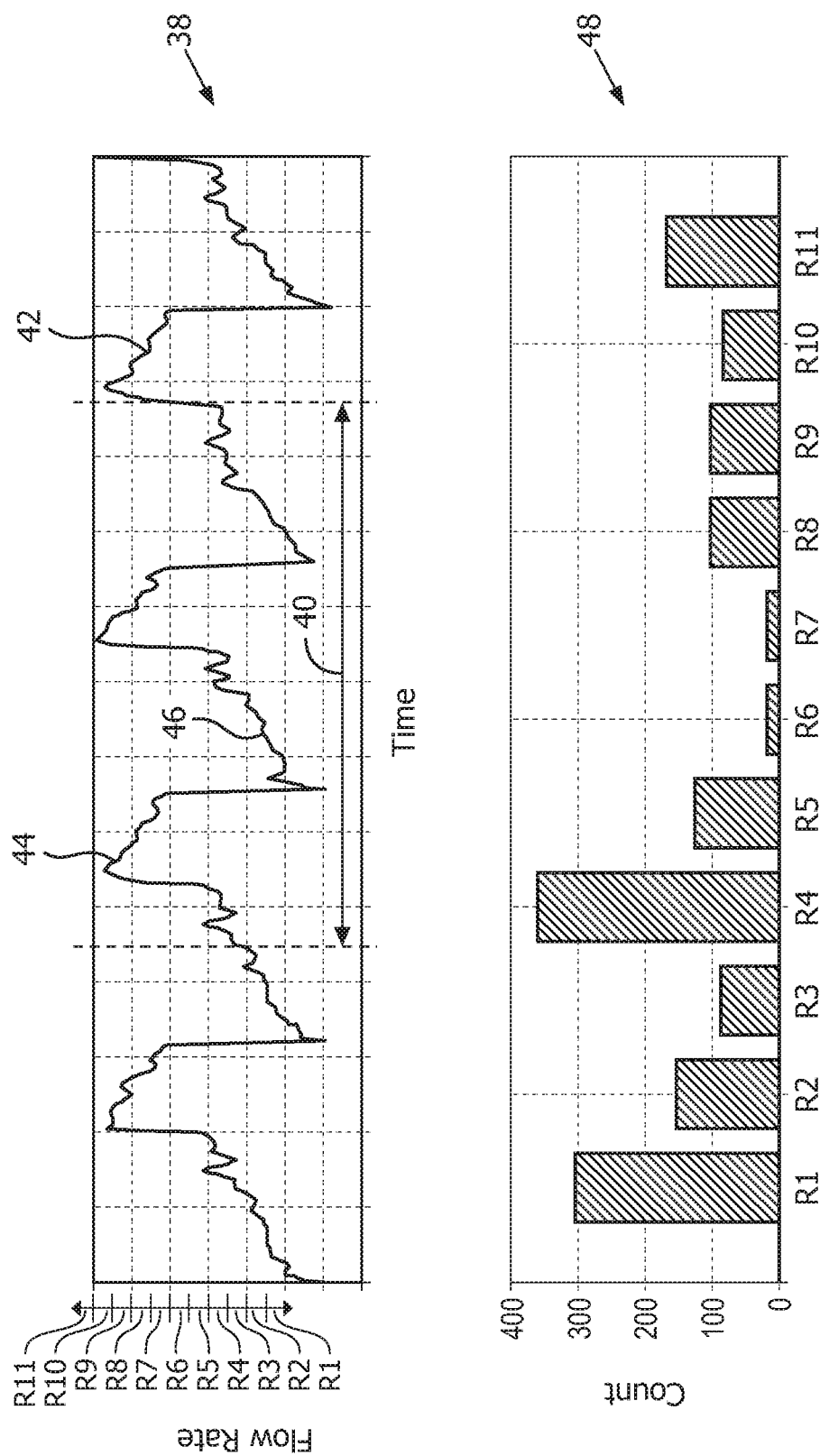
FIG. 2 illustrates plots of gas parameters of the pressurized flow of breathable gas over time, and a population distribution histogram illustrating the distribution of gas parameter values within given ranges.

The flow rate parameter values indicate the flow rate of the pressurized flow of breathable gas generated by pressure generator 12 during the individual sampling intervals. By way of illustration, FIG. 2 illustrates plots of gas parameters of the pressurized flow of breathable gas over time (e.g., represented by output signals of one or more sensors 32). Plot 38 provides a graphical representation of flow rate parameter values 42 (e.g., as represented by output signals of one or more sensors). In plot 38, the oscillating flow rate parameter values 42 of the pressurized flow of breathable gas forms peaks 44 which represent inspiratory flow phases of the subject (e.g., inhalation), and troughs 46 which represent expiratory flow phases of the subject (e.g., exhalation). Transitions between expiratory flow phases and inspiratory flow phases are determined by transitions between troughs 46 and peaks 44. The transitions represent zero subject flow rate. In plot 38, a first determination period 40 is provided. First determination period 40 may be time duration determined by one or more of the methods discussed above, and/or other time duration. First determination period 40 may be selected to encompass several breaths of the subject.

Returning to FIG. 1, grouping module 18 is configured to group (e.g., cluster) the gas parameters of the pressurized flow of breathable gas (e.g., represented by output signals of one or more sensors 32) into flow rate ranges. The flow rate ranges may be determined in a variety of ways. The flow rate ranges may be determined from the minimum and maximum flow rate parameter values relating to the output signals of sensor 32, and/or other determination.

The determination period of gas parameter sampling may be examined for a minimum (Qmin) and a maximum (Qmax) gas parameter value. These values may be used to define equal bounds (W) of the individual flow rate ranges. Initially, a total number of flow rate ranges is chosen. The total number of flow rate ranges may be any number. For example, experimentation has shown that a total of eleven flow rate ranges is sufficient. The value range between the minimum and maximum gas parameter values is divided by the number of flow rate ranges to determine equal bounds of the individual flow rate ranges. Therefor determining bounds of the flow rate ranges uses the following equation:

$$W=(Q\max-Q\min)/(\text{\# of rate ranges}).$$

By way of illustration, returning to FIG. 2 illustrating plots of gas parameters of the pressurized flow of breathable gas over time (e.g., represented by output signals of one or more sensors 32). Plot 38 provides a graphical representation of sampled flow rate parameter values 42 (e.g., as represented by output signals of one or more sensors). A total of eleven flow rate ranges may be selected for grouping the flow rate parameter values. A maximum flow rate parameter value (Qmax) and minimum flow rate parameter value (Qmin) may be obtained from plot 38. The bounds (W) of the eleven flow rate ranges may be determined by; W=(Qmax−Qmin)/11. As shown in plot 38, eleven flow rate ranges, R1-R11 are provided, wherein each range R1-R11 encompasses a flow rate bound of W.

It is noted that refinements to the establishment of the flow rate ranges R1-R11 may be performed. For example, in the case where the calculation of the bounds, W, is distorted due to one or more outlying flow rate parameter values 42 associated with the output signals generated by the one or more sensors (e.g., due to noise and/or other reasons). Refinements may include re-defining the first and last flow rate ranges to not have a bound of W, but instead are defined as "all flow rate parameter values below" and "all flow rate parameter values above", respectively, the bound of the adjoining flow rate range. Refinements may be performed using other techniques.

Returning to FIG. 1, quantification module 20 is configured to quantify the number of flow rate parameter values within the bounds of the individual flow rate ranges within the sampling determination period. Quantification of the number of flow rate parameter values within the bounds of the individual flow rate ranges will indicate a population distribution of the flow rate parameter values with respect to the flow rate ranges. Quantification of the number of flow rate parameter values within the bounds of the individual flow rate ranges may indicate one or more flow rate ranges with the highest populations of flow rate parameter values. The flow rate range(s) with the highest population of flow rate parameter values may indicate that the flow rate range includes the flow rate parameter value corresponding to zero subject flow rate.

By way of illustration, returning to FIG. 2 plot 48 illustrates a sampled population distribution histogram of the flow rate ranges (R1-R11). The depicted magnitude of the flow rate ranges (R1-R11) indicates the number (e.g., count) of flow rate parameter values within the respective flow rate range (R1-R11).

Returning to FIG. 1, correlation module 22 is configured to correlate the population distribution of the flow rate ranges with a correlation template of known flow rate range distributions to confirm the validity of the sampled population distribution for determining the flow rate parameter value corresponding to zero subject flow rate. Through a correlation (e.g., by a similar matching and/or substantially similar matching) by correlation module 22 of the population distribution of the sampled flow rate parameter values obtained from quantification module 20 with the template of known flow rate range distributions, the sampled population distribution can be validated as having one or more flow rate ranges which contain the flow rate parameter value corresponding to zero subject flow rate. Identifying one or more flow rate ranges having the highest number of flow rate parameter values (e.g., largest population of values) may indicate that the identified flow rate range(s) includes the flow rate parameter value corresponding to zero patient flow rate, if validated by a successful correlation with one of the known distributions.

Figure 3:
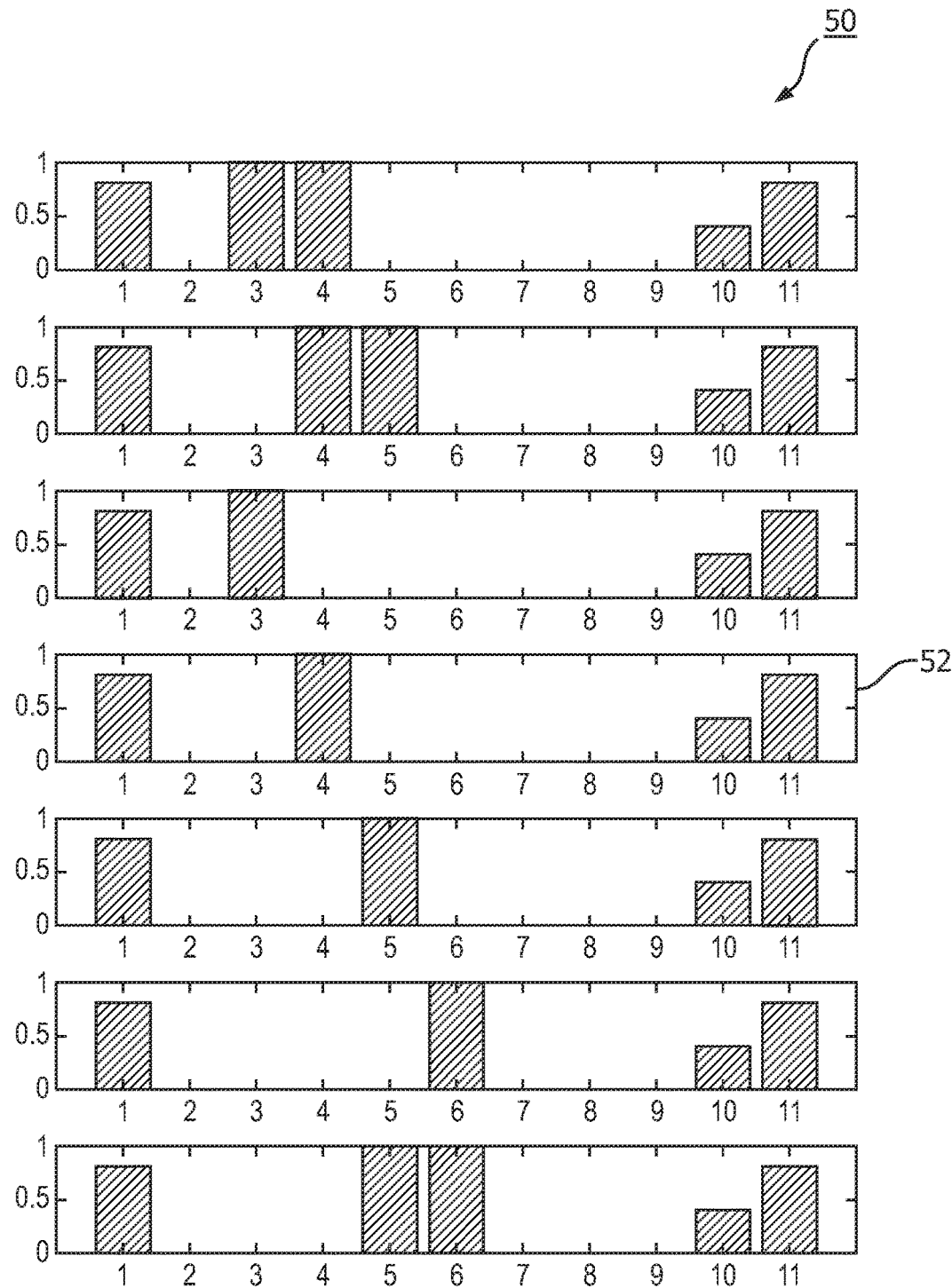
FIG. 3 is a correlation template depicting multiple normalized population distribution histograms of known population distributions.

By way of illustration, FIG. 3 shows an example of a correlation template 50, depicting multiple normalized flow rate range distributions. The distributions of flow rate ranges of correlation template 50 may be determined through experimentation and/or other techniques. The distributions are generally normalized by the flow rate range of the highest magnitude (with relatively low magnitude ranges zeroed out). For example, distribution 52 depicts range "4" being the dominant range. Therefor a correlation with distribution 52 would validate that the sampled population distribution's flow rate range in position "4" contains the highest number of flow rate parameter values, and would contain the flow parameter value corresponding to zero subject flow rate. For the sampled population distribution of plot 48 from FIG. 2, correlation may determine a match (e.g., a match of relative magnitudes, with low magnitude flow rate ranges zeroed out) with distribution 52, since flow rate range R4 of FIG. 2 is the dominant flow rate range within the distribution similar to range "4" from distribution 52 of FIG. 3. Therefor this correlation validates that sampled distribution contains at least one flow rate ranging including a flow rate parameter value corresponding to zero subject flow rate, namely flow rate range R4 of plot 48 from FIG. 2 is the range which contains the flow rate parameter value corresponding to zero subject flow rate.

Returning to FIG. 1, zero flow rate determination module 24 is configured to determine from the flow rage range identified by quantification module 20, the flow rate parameter value that corresponds to zero subject flow rate. Determining the flow rate parameter value that corresponds to zero subject flow rate may be accomplished in a variety of ways. Determination may be based on the quantifications obtained from quantification module 20. Determination may be based on the correlation from correlation module 22. Determination may be based on one or more of the quantifications obtained from quantification module 20, the correlation from correlation module 22, and/or other techniques.

Determining the flow rate parameter value that corresponds to zero subject flow rate may be based on the quantifications obtained from quantification module 20. Zero flow rate determination module 24 may determine that the flow rate parameter value corresponding to zero subject flow rate is a flow rate parameter value within the bounds of the flow rate range which has the largest magnitude (e.g., highest count of flow rate parameter values within the bound of the flow rate range). For example, returning to FIG. 2, the flow rate parameter value corresponding to zero subject flow rate is within the bound of flow rate parameter values may be determined to be within flow rate range R4 (e.g., the flow rate range from R1-R11 with largest magnitude).

Returning to FIG. 1, determining the flow rate parameter value that corresponds to zero subject flow rate may be based on the correlation from correlation module 22, and the quantifications obtained from quantification module 20. Zero flow rate determination module 24 may determine that the flow rate parameter value corresponding to zero subject flow rate is a flow rate parameter value within the bounds of the flow rate range which has the largest magnitude, wherein this is thereafter validated by the correlation from correlation module 22.

By way of example, in FIG. 2, an initial identification of the flow rate range containing the flow rate parameter value corresponding to zero subject flow rate may be flow rate range R4 (e.g., the flow rate range from R1-R11 with largest magnitude). In FIG. 3, distribution 52 shows range "4" as the dominant range of the distribution, which correlates (e.g., matches and/or substantially matches in relative magnitudes) with the sampling distribution shown plot 48 of FIG. 2. Therefore, the initial identification of flow rate range R4 is validated by the correlation.

Returning to FIG. 1, once the flow rate range containing the flow rate parameter value corresponding to zero subject flow rate is identified by zero flow rate determination module 24 by one or more of the techniques described above, zero flow rate determination module 24 calculates the flow rate parameter value corresponding to zero subject flow rate. Calculation can be accomplished in a variety of ways. Calculation can include calculating an average of the flow rate parameter values from the identified flow rate range(s). Calculation can include calculating a weighted average of the flow rate parameter values from the identified flow rate ranges if more than one flow rate range is identified. By way of illustration, returning to FIG. 2, an average of the flow rate parameter values within flow rate range R4 may be calculated. The calculated value can then be used to update the leak estimation method (e.g., leak estimation algorithm) being carried out by leak estimation module 15 of FIG. 1.

In FIG. 1, zero flow rate determination module 24 may be further configured such that responsive to a failure to correlate the flow rate ranges with the correlation template of known flow rate range distributions by correlation module 22, leak estimation module 15 selects an alternative method for correcting the leak estimation method being carried out by leak estimation module 15 (e.g., leak estimation algorithm and/or other method or technique). Alternative methods may include simplified leak estimation methods and/or other known leak estimation methods and/or techniques.

Failure to correlate the flow rate ranges with the correlation template of known flow rate range distributions by correlation module 22 may also indicate that the leak estimation method being used by leak estimation module 15 is correct, and zero flow rate determination module 24 may determine that no updates to the method employed by leak estimation module 15 are needed.

Figure 4:
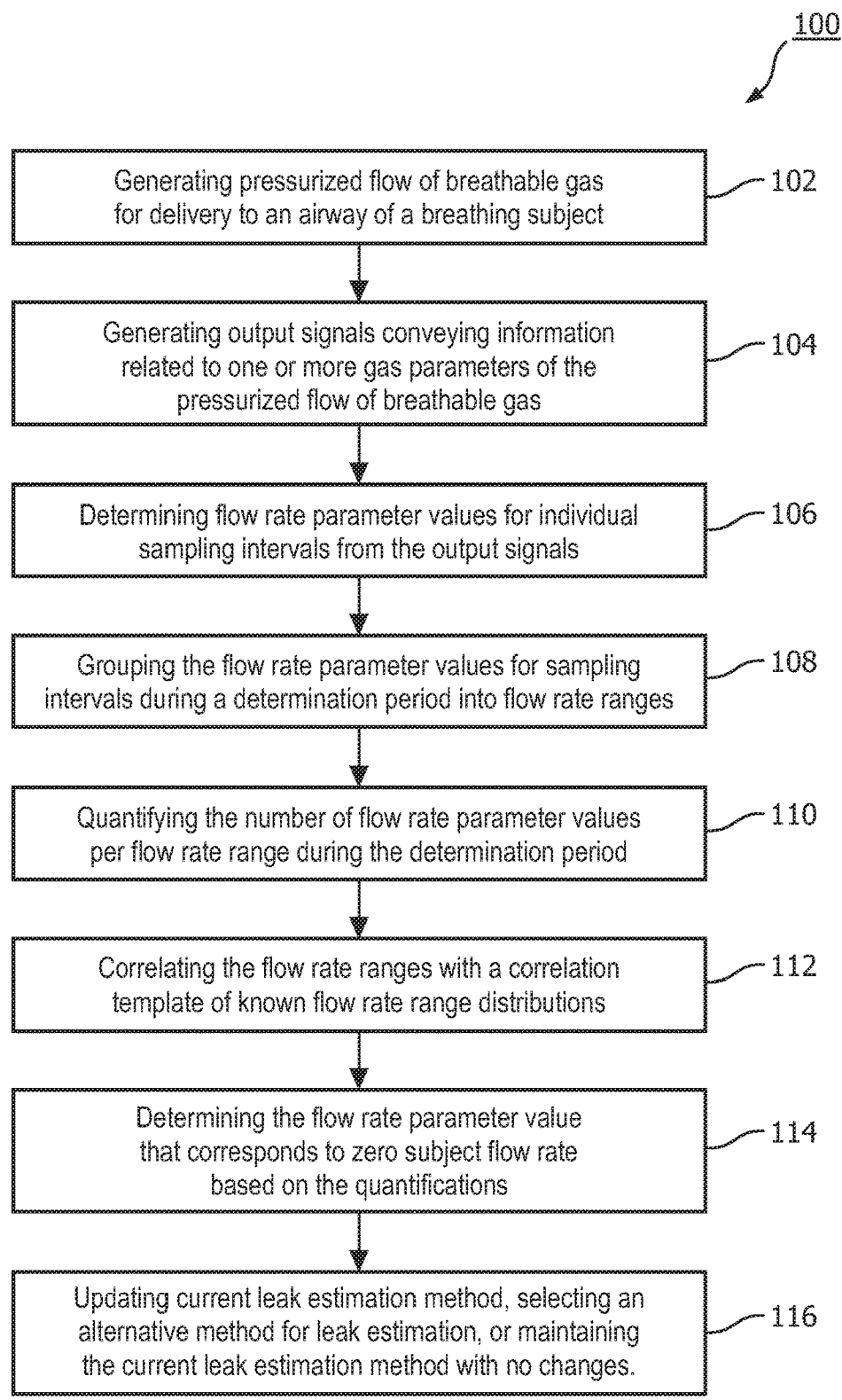
FIG. 4 is a method for determining the flow rate of pressurized flow of breathable gas generated in respiratory devices which corresponds to zero subject flow.

FIG. 4 illustrates a method 100 for determining zero subject flow rate for correcting leak estimation in respiratory devices. The determination may include using a pressure generator configured to generate pressurized flow of breathable gas to a subject, a conduit for communicating pressurized flow from the pressure generator to a subject, an interface appliance to communicate the pressurized flow to the airway of the subject, one or more sensors configured to generate output signals conveying information related to one or more gas parameters of the pressurized flow, one or more processors configured to execute computer modules, a power source, a user interface, electronic storage, and/or other components. The operations of method 100 presented below are intended to be illustrative. In some embodiments, method 100 may be accomplished with one or more additional operations not described, and/or without one or more of the operations discussed. Additionally, the order in which the operations of method 100 are illustrated in FIG. 4 and described below is not intended to be limiting.

In some embodiments, method 100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 100 in response to instructions stored electronically on an electronic storage medium. The one or more processing devices may include one or more devices configured through hardware, firmware, and/or software to be specifically designed for execution of one or more of the operations of method 100.

At an operation 102, the pressurized flow of breathable gas is generated with the pressure generator and communicated to the airway of the subject. In some embodiments, operation 102 is performed by a pressure generator the same as or similar to pressure generator 12 (shown in FIG. 1 and described herein).

At an operation 104, one or more output signals conveying information related to one or more gas parameters of the pressurized flow of breathable gas are generated with the one or more sensors. In some embodiments, operation 104 is performed by sensors the same as or similar to sensors 32 (shown in FIG. 1 and described herein.)

At an operation 106, flow rate parameter values for individual sampling intervals from the output signals are determined. The flow rate parameter values indicate flow rate of the pressurized flow of breathable gas during the individual sampling intervals. In some embodiments, operation 106 is performed by a parameter module the same as or similar to parameter module 16 (shown in FIG. 1 and described herein).

At an operation 108, flow rate parameter values for sampling intervals over determination period are grouped into flow rate ranges. In some embodiments, operation 108 is performed by a grouping module the same as or similar to grouping module 18 (shown in FIG. 1 and described herein).

At an operation 110, the number of flow rate parameter values within each flow rate range is quantified. The quantification may indicate a flow rate parameter population distribution with respect to the flow rate ranges. In some embodiments, operation 110 is performed by a quantification module the same as or similar to quantification module 20 (shown in FIG. 1 and described herein).

At an operation 112 the flow rate parameter population distribution is correlated with a correlation template of known flow rate range distributions such that responsive to the correlation, identification of one or more flow rate ranges which contain the flow rate parameter value corresponding to zero subject flow rate is validated. In some embodiments, operation 112 is performed by a correlation module the same as or similar to correlation module 22 (shown in FIG. 1 and described herein).

At an operation 114, the flow rate parameter value corresponding to zero subject flow rate is calculated. In some embodiments, operation 114 is performed by a zero flow rate determination module the same as or similar to zero subject determination module 24 (shown in FIG. 1 and described herein).

At an operation 116, one of the following actions is perform: updating the current leak estimation method based on the calculated flow rate parameter value corresponding to zero subject flow rate, selecting an alternative method for leak estimation, or maintaining the current leak estimation method with no changes. In some embodiments, operation 116 is performed by a zero flow rate determination module the same as or similar to zero subject determination module 24 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for determining flow rate of a pressurized flow of breathable gas generated in a respiratory device, the determination of flow rate providing a basis for corrections to a leak estimation method employed by the respiratory device, the system comprising:
   a pressure generator configured to generate pressurized flow of breathable gas for delivery to an airway of a breathing subject;
   one or more sensor configured to generate output signals conveying information related to one or more gas parameters of the pressurized flow of breathable gas;
   one or more processors configured to execute computer program modules, the computer program modules comprising:
      a parameter module configured to determine flow rate parameter values for individual sampling intervals from the output signals of the one or more sensors, the flow rate parameter values indicating flow rate of the pressurized flow of breathable gas during the individual sampling intervals,
      a grouping module configured to group the flow rate parameter values for sampling intervals during a determination period into flow rate ranges, wherein the flow rate ranges are determined based on a maximum flow rate parameter value and a minimum flow rate parameter value for the determination period,
      a quantification module configured to quantify the number of flow rate parameter values per flow rate range during the determination period, and
      a zero flow rate determination module configured to determine a flow rate parameter value that corresponds to zero subject flow rate based on the quantified numbers of flow rate parameter values per flow rate range; and
   a correlation module configured to correlate the distribution of flow rate parameter values in the flow rate ranges with a correlation template of known distributions of flow rate parameter values in the flow rate ranges, such that responsive to the correlation, identification of one or more flow rate ranges which contain the flow rate parameter value corresponding to zero subject flow rate is validated.

2. The system of claim 1, wherein the zero flow rate determination module is further configured such that responsive to a failure to correlate the flow rate ranges with the correlation template of known flow rate range distributions by the correlation module, the zero flow rate determination module selects an alternative method for correcting leak estimation.

3. A system for determining flow rate of a pressurized flow of breathable gas generated in a respiratory device, the determination of flow rate providing a basis for corrections to a leak estimation method employed by the respiratory device, the system comprising:

a pressure generator configured to generate pressurized flow of breathable gas for delivery to an airway of a breathing subject;

one or more sensor configured to generate output signals conveying information related to one or more gas parameters of the pressurized flow of breathable gas; and one or more processors configured to execute computer program modules, the computer program modules comprising:

a parameter module configured to determine flow rate parameter values for individual sampling intervals from the output signals of the one or more sensors, the flow rate parameter values indicating flow rate of the pressurized flow of breathable gas during the individual sampling intervals, a grouping module configured to group the flow rate parameter values for sampling intervals during a determination period into flow rate ranges, wherein the flow rate ranges are determined based on a maximum flow rate parameter value and a minimum flow rate parameter value for the determination period, a quantification module configured to quantify the number of flow rate parameter values per flow rate range during the determination period, and a zero flow rate determination module configured to determine a flow rate parameter value that corresponds to zero subject flow rate based on the quantified numbers of flow rate parameter values per flow rate range, wherein the zero flow rate determination module is further configured such that determining the flow rate parameter value that corresponds to zero flow rate includes identifying one or more flow rate ranges having the highest number of flow rate parameter values, validating that the identified one or more flow rate ranges contain the flow rate parameter value corresponding to zero subject flow rate, and computing an average flow rate parameter value from the flow rate parameter values of the identified one or more flow rate ranges.

4. The system of claim 3, wherein the zero flow rate determination module is further configured such that computing the average flow rate parameter value includes computing a weighted average from the flow rate parameter values of the identified one or more flow rate ranges.

5. A method for determining flow rate of a pressurized flow of breathable gas generated in a respiratory device, the determination of flow rate providing a basis for corrections to a leak estimation method employed by the respiratory device, the method for determining flow rate comprising:

generating the pressurized flow of breathable gas for delivery to an airway of a breathing subject;

generating output signals conveying information related to one or more gas parameters of the pressurized flow of breathable gas;

determining flow rate parameter values for individual sampling intervals from the output signals, the flow rate parameter values indicating flow rate of the pressurized flow of breathable gas during the individual sampling intervals;

grouping the flow rate parameter values for sampling intervals during a determination period into flow rate ranges, wherein the flow rate ranges are determined based on a maximum flow rate parameter value and a minimum flow rate parameter value for the determination period;

quantifying the number of flow rate parameter values per flow rate range during the determination period;

determining a flow rate parameter value that corresponds to zero subject flow rate based on the quantified numbers of flow rate parameter values per flow rate range; and correlating the flow rate ranges with a correlation template of known flow rate range distributions, such that responsive to the correlation, identification of one or more flow rate ranges which contain the flow rate parameter value corresponding to zero subject flow rate is validated.

6. The method of claim 5, further comprising; responsive to a failure to correlate the flow rate ranges with the correlation template of known flow rate range distributions, the zero flow rate determination module selects an alternative method for correcting leak estimation.

7. A method for determining flow rate of a pressurized flow of breathable gas generated in a respiratory device, the determination of flow rate providing a basis for corrections to a leak estimation method employed by the respiratory device, the method for determining flow rate comprising:

generating the pressurized flow of breathable gas for delivery to an airway of a breathing subject;

generating output signals conveying information related to one or more gas parameters of the pressurized flow of breathable gas;

determining flow rate parameter values for individual sampling intervals from the output signals, the flow rate parameter values indicating flow rate of the pressurized flow of breathable gas during the individual sampling intervals;

grouping the flow rate parameter values for sampling intervals during a determination period into flow rate ranges, wherein the flow rate ranges are determined based on a maximum flow rate parameter value and a minimum flow rate parameter value for the determination period;

quantifying the number of flow rate parameter values per flow rate range during the determination period;

determining a flow rate parameter value that corresponds to zero subject flow rate based on the quantified numbers of flow rate parameter values per flow rate range, wherein determining the flow rate parameter value that corresponds to zero flow rate based on the quantifications includes identifying one or more flow rate ranges having the highest number of flow rate parameter values, validating that the identified one or more flow rate ranges contain the flow rate parameter value corresponding to zero subject flow rate, and computing an average flow rate parameter value from the flow rate parameter values of the identified one or more flow rate ranges.

8. The method of claim 7, wherein computing an average flow rate parameter value comprises computing a weighted average from the flow rate parameter values of the one or more identified flow rate ranges containing the flow rate parameter value corresponding to zero flow rate.

9. A system for determining a flow rate of a pressurized flow of breathable gas generated in a respiratory device, the determination of flow rate providing a basis for corrections to a leak estimation method employed by the respiratory device, the system comprising:

means for generating pressurized flow of breathable gas for delivery to an airway of a breathing subject;

means for generating output signals conveying information related to one or more gas parameters of the pressurized flow of breathable gas;

means for determining flow rate parameter values for individual sampling intervals from the output signals, the flow rate parameter values indicating flow rate of the pressurized flow of breathable gas during the individual sampling intervals;

means for grouping the flow rate parameter values for sampling intervals during a determination period into flow rate ranges, wherein the flow rate ranges are determined based on a maximum flow rate parameter value and a minimum flow rate parameter value for the determination period;

means for quantifying the number of flow rate parameter values per flow rate range during the determination period;

means for determining a flow rate parameter value that corresponds to a zero subject flow rate based on the quantified numbers of flow rate parameter values per flow rate range; and means for correlating the flow rate ranges with a correlation template of known flow rate range distributions, such that responsive to the correlation, identification of one or more flow rate ranges which contain the flow rate parameter value corresponding to zero subject flow rate is validated.

10. The system of claim 9, wherein the means for determining the flow rate parameter value is further configured such that responsive to a failure to correlate the flow rate ranges with the correlation template of known flow rate range distributions by the means for correlating the means for determining the flow rate parameter value selects an alternative method for correcting leak estimation.

11. A system for determining a flow rate of a pressurized flow of breathable gas generated in a respiratory device, the determination of flow rate providing a basis for corrections to a leak estimation method employed by the respiratory device, the system comprising:

means for generating pressurized flow of breathable gas for delivery to an airway of a breathing subject;

means for generating output signals conveying information related to one or more gas parameters of the pressurized flow of breathable gas;

means for determining flow rate parameter values for individual sampling intervals from the output signals, the flow rate parameter values indicating flow rate of the pressurized flow of breathable gas during the individual sampling intervals;

means for grouping the flow rate parameter values for sampling intervals during a determination period into flow rate ranges, wherein the flow rate ranges are determined based on a maximum flow rate parameter value and a minimum flow rate parameter value for the determination period;

means for quantifying the number of flow rate parameter values per flow rate range during the determination period; and means for determining a flow rate parameter value that corresponds to a zero subject flow rate based on the quantified numbers of flow rate parameter values per flow rate range, wherein the means for determining the flow rate parameter value is further configured such that determining the flow rate parameter value that corresponds to zero flow rate includes identifying one or more flow rate ranges having the highest number of flow rate parameter values, validating that the identified one or more flow rate ranges contain the flow rate parameter value corresponding to zero subject flow rate, and computing an average flow rate parameter value from the flow rate parameter values of the identified one or more flow rate ranges.

12. The system of claim 11, wherein computing the average flow rate parameter value includes computing a weighted average from the flow rate parameter values of the identified one or more flow rate ranges validated by the means for determining the flow rate parameter value to contain the flow rate parameter value corresponding to zero flow rate.

* * * * *